(12) United States Patent
Charles

(10) Patent No.: US 11,931,297 B2
(45) Date of Patent: Mar. 19, 2024

(54) GLARE REDUCTION ENDOILLUMINATORS

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 94 days.

(21) Appl. No.: 16/897,674

(22) Filed: Jun. 10, 2020

(65) Prior Publication Data
US 2020/0390598 A1     Dec. 17, 2020

Related U.S. Application Data

(60) Provisional application No. 62/861,396, filed on Jun. 14, 2019.

(51) Int. Cl.
*A61F 9/009* (2006.01)
*G02C 7/12* (2006.01)
*A61F 9/008* (2006.01)

(52) U.S. Cl.
CPC ............... *A61F 9/009* (2013.01); *G02C 7/12* (2013.01); *A61F 2009/00863* (2013.01); *A61F 2009/00872* (2013.01)

(58) Field of Classification Search
CPC ............ A61F 9/009; A61F 2009/00863; A61F 2009/00872
See application file for complete search history.

(56) References Cited

U.S. PATENT DOCUMENTS

| 5,973,781 | A  | 10/1999 | Moeller |
| 7,050,672 | B1 | 5/2006  | Matsumoto |
| 7,189,226 | B2 | 3/2007  | Auld |
| 7,612,880 | B2 | 11/2009 | Chipman |
| 7,618,177 | B2 | 11/2009 | Cazzini |
| 8,371,695 | B2 | 2/2013  | Papac |
| 8,480,279 | B2 | 7/2013  | Papac |
| 8,496,331 | B2 | 7/2013  | Smith |
| 8,641,274 | B2 | 2/2014  | Omichi |
| 8,807,751 | B2 | 8/2014  | Kahn |
| 9,072,587 | B2 | 7/2015  | Smith |
| 9,538,914 | B2 | 1/2017  | Hauger |

(Continued)

FOREIGN PATENT DOCUMENTS

| DE | 102018118253 A1 | * 1/2020 | ............ F16F 15/145 |
| WO | 2015067293 A1 | 5/2015 | |

OTHER PUBLICATIONS

Alcon Global Vitreoretinal Product Catalog, dated Feb. 2014, pp. 1 and 25-48.

(Continued)

*Primary Examiner* — Nathan J Jenness
*Assistant Examiner* — Skylar Lindsey Christianson
(74) *Attorney, Agent, or Firm* — PATTERSON + SHERIDAN, LLP

(57) ABSTRACT

Certain embodiments describe an endoilluminator having a tube that includes an interior compartment between a proximal end and a distal end of the tube, wherein the distal end of the tube is configured to be inserted into an eye. The endoilluminator also includes a handpiece coupled to a light source and the proximal end of the tube, wherein the endoilluminator is configured to filter an incident component of light transmitted by the light source and emit a polarized component of the transmitted light through the distal end of the tube.

11 Claims, 6 Drawing Sheets

(56) References Cited

U.S. PATENT DOCUMENTS

| | | | |
|---|---|---|---|
| 10,016,248 B2 | 7/2018 | Mirsepassi | |
| 10,307,290 B2 | 6/2019 | Kern | |
| 10,426,339 B2 | 10/2019 | Papac | |
| 10,849,789 B2 | 12/2020 | Dewey | |
| 2005/0078910 A1 | 4/2005 | Hickingbotham | |
| 2006/0126679 A1* | 6/2006 | Brennan, III | G02B 6/02361 |
| | | | 372/30 |
| 2008/0291460 A1* | 11/2008 | Khatchaturov | G01J 1/4228 |
| | | | 356/478 |
| 2009/0030406 A1* | 1/2009 | Hickingbotham | A61B 90/30 |
| | | | 606/4 |
| 2012/0188360 A1* | 7/2012 | Okamoto | G02B 21/365 |
| | | | 348/79 |
| 2013/0081253 A1* | 4/2013 | Smith | B23P 11/025 |
| | | | 29/447 |
| 2014/0362343 A1* | 12/2014 | Hauger | G02B 21/16 |
| | | | 351/206 |
| 2016/0113722 A1* | 4/2016 | Heeren | A61B 3/0008 |
| | | | 600/249 |
| 2017/0231711 A1* | 8/2017 | Abt | A61B 90/361 |
| | | | 351/206 |
| 2018/0055596 A1 | 3/2018 | Johnson | |
| 2018/0172970 A1* | 6/2018 | Themelis | A61B 1/00186 |
| 2018/0299616 A1* | 10/2018 | Nagano | G02B 6/032 |
| 2019/0175407 A1 | 6/2019 | Bacher | |
| 2019/0209372 A1 | 7/2019 | Farley | |
| 2021/0164900 A1* | 6/2021 | Zerulla | G01N 21/553 |

OTHER PUBLICATIONS https://en.wikipedia.org/w/index.php?title=Polarization-maintaining_optical fiber&oldid=846377473 (dated Jun. 18, 2018) (accessed on Jan. 11, 2021), 3 pages.

https://web.archive.org/web/20160410013304/https://www.thorlabs.com/newgrouppage9.cfm?objectgroup_ID=5922, Web Archive dated Apr. 10, 2016 (accessed on Jan. 11, 2021), 3 pages.

https://web.archive.org/web/20160412205332/http://www.thorlabs.com/newgrouppage9.cfm?objectgroup_ID=1596 (Web archive dated Apr. 12, 2016) (accessed (Jan. 11, 2021), 7 pages.

https://web.archive.org/web/20180713011732/http://www.fujikura.co.jp/eng/resource/pdf/16pnb04.pdf, dated Feb. 2018, (Web archive dated Jul. 13, 2018) (accessed Jan. 11, 2021), 44 pages.

https://web.archive.org/web/20190519231952/http://www.imagineoptix.com/resources/technology-comparisons/ (Web archive dated May 19, 2019) (accessed Jan. 12, 2021), 8 pages.

\* cited by examiner

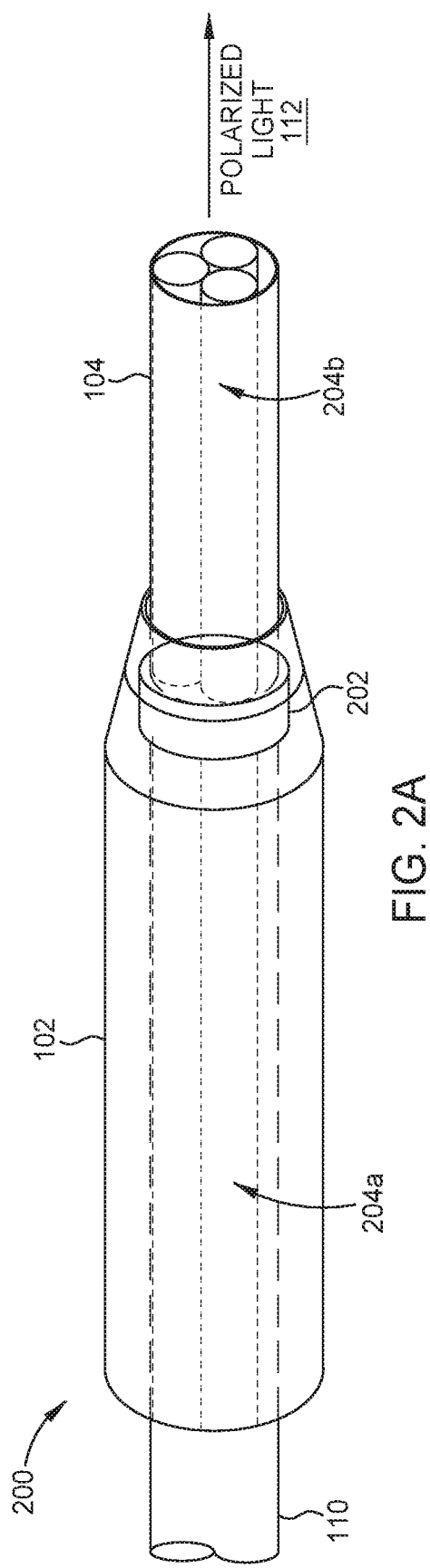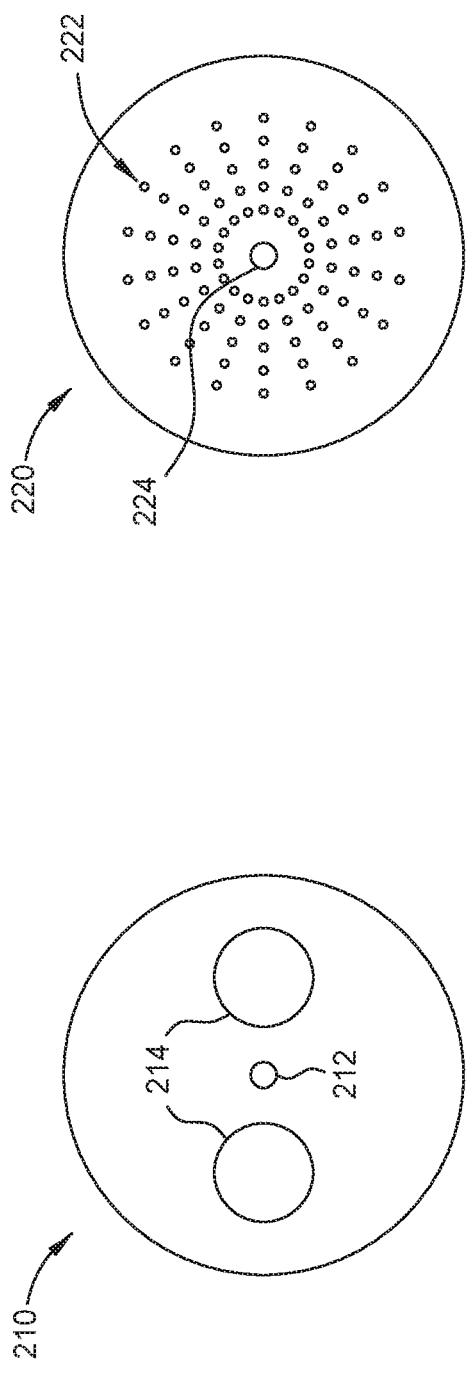
FIG. 2A
FIG. 2B
FIG. 2C

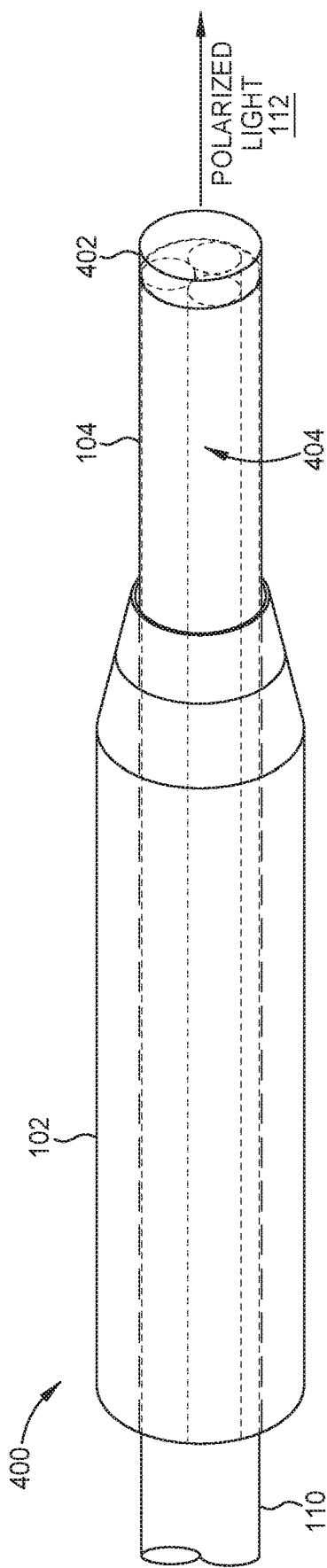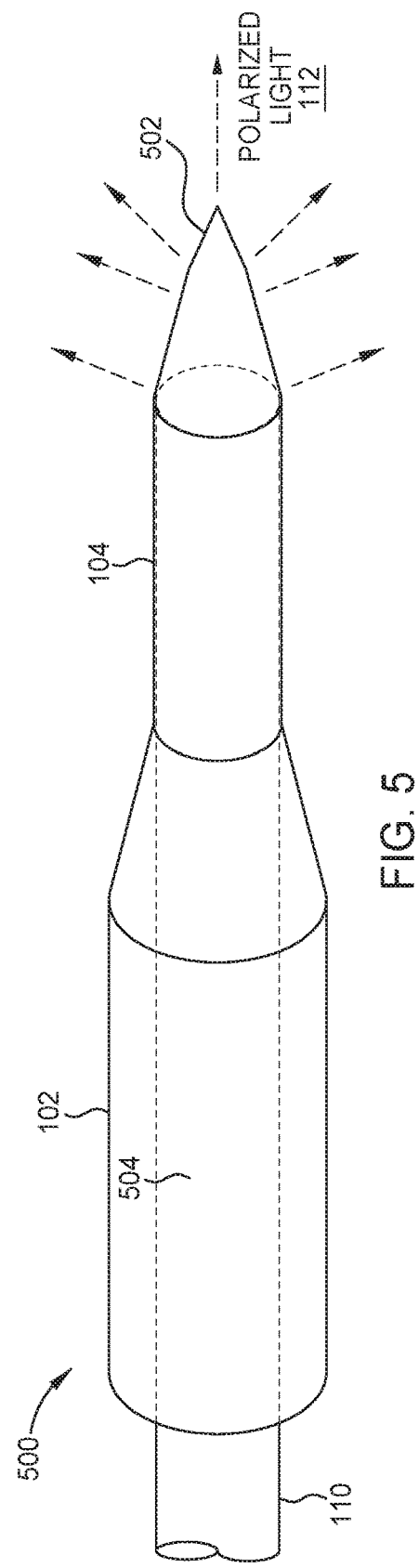

GLARE REDUCTION ENDOILLUMINATORS

PRIORITY CLAIM

This application claims the benefit of priority of U.S. Provisional Patent Application Ser. No. 62/861,396 titled "GLARE REDUCTION ENDOILLUMINATORS," filed on Jun. 14, 2019, whose inventor is Steven T. Charles, which is hereby incorporated by reference in its entirety as though fully and completely set forth herein.

TECHNICAL FIELD

This application relates to ophthalmic illuminators and more particularly to polarized ophthalmic illumination.

BACKGROUND

Ophthalmic illuminators allow a surgeon to illuminate the interior of an eye such as the vitreous and the retina during surgical procedures. For example, an ophthalmic illuminator (endoilluminator) includes a handpiece coupled to a shaft or "tube" configured to be inserted into the eye through a cannula and sclerotomy. In some cases, the endoilluminator includes a fiber optic element within a bore of the tube. By driving a proximal end of the fiber optic element with a suitable light source, light emitted from a distal end of the fiber illuminates the desired portion of the eye during a surgical procedure. A user (e.g., an ophthalmic surgeon) may illuminate the eye with the endoilluminator while using an ophthalmic microscope or a digital visualization system (e.g., Alcon NGENUITY(R) "heads-up surgery" visualization system) to observe the eye when performing surgical maneuvers.

One disadvantage exhibited by endoilluminators is glare. Glare results when light from the endoilluminator is scattered and reflected such that the light interferes with the surgeon's visualization of the vitreous, retina and pathology. Glare is unwanted stray light that provides no useful illumination, and either distracts the surgeon or obscures an object under observation. For example, cataracts, intraocular lenses, corneal edema and opacities, cloudy vitreous, and the like, can scatter light produced by the endoilluminator. Other sources of glare include the highly reflective properties of eye tissue (e.g., the retina surface) especially after fluid-air exchange and after liquid perfluorocarbon or silicone oil injection.

Typically, glare can only be corrected by reducing the total illumination, thereby reducing the amount of light available for surgery by the surgeon. As such, there is an inherent tradeoff with current endoilluminator devices between sufficient light for performing surgery and glare interfering with surgical visualization.

BRIEF SUMMARY

The present disclosure relates generally to polarized ophthalmic illumination.

Certain aspects provide an endoilluminator for ophthalmic surgery, including a hollow, typically stainless steel tube, having an interior compartment between a proximal end and a distal end of the tube, wherein the distal end of the tube is configured to be inserted into an eye. The endoilluminator also includes a handpiece coupled to a light source and the proximal end of the tube, wherein the endoilluminator is configured to filter an incident component of light transmitted by the light source and emit a polarized component of the transmitted light through the distal end of the tube.

Certain aspects provide a system for ophthalmic surgery including an endoilluminator and a microscope. The endoilluminator includes a tube including an interior compartment between a proximal end and a distal end of the tube, wherein the distal end of the tube is configured to be inserted into an eye. The endoilluminator also includes a handpiece coupled to a light source and the proximal end of the tube, wherein the endoilluminator is configured to filter a first incident component of light transmitted by the light source and emit a first polarized component of the transmitted light through the distal end of the tube. The microscope includes a filter configured to receive a reflection of the first polarized component of the transmitted light from the eye, filter a second incident component of the received reflection, and pass a second polarized component of the transmitted light.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIG. 2A illustrates a side perspective view of an endoilluminator with a light-polarizing element at a distal end of the tube, according to some embodiments of the present disclosure.

FIG. 2B illustrates a cross-sectional view of an example polarization-maintaining fiber for use in the endoilluminator of FIG. 2A, according to some embodiments of the present disclosure.

FIG. 2C illustrates a cross-sectional view of an example of a photonic crystal polarization maintaining fiber for use in the endoilluminator of FIG. 2A, according to some embodiments of the present disclosure.

FIG. 4 illustrates a side perspective view of an endoilluminator with a light-polarizing filter at the tip of the tube, according to some embodiments of the present disclosure.

FIG. 5 illustrates a side perspective view of an endoilluminator with a chandelier tip, according to some embodiments of the present disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods. As described below, the figures herein each illustrate apparatus and methods for reducing glare and improving surgical visualization of a patient's eye through microscopy.

As used herein, the term "proximal" refers to a location with respect to a device or portion of the device that, during normal use, is closest to the clinician using the device and farthest from the patient in connection with whom the device is used. Conversely, the term "distal" refers to a location with respect to the device or portion of the device that, during normal use, is farthest from the clinician using the device and closest to the patient in connection with whom the device is used. For example, the terms "distal" and "proximal" as used herein may refer to a relative location with respect to an endoilluminator, a microscope, or a portion thereof.

Figure 1:
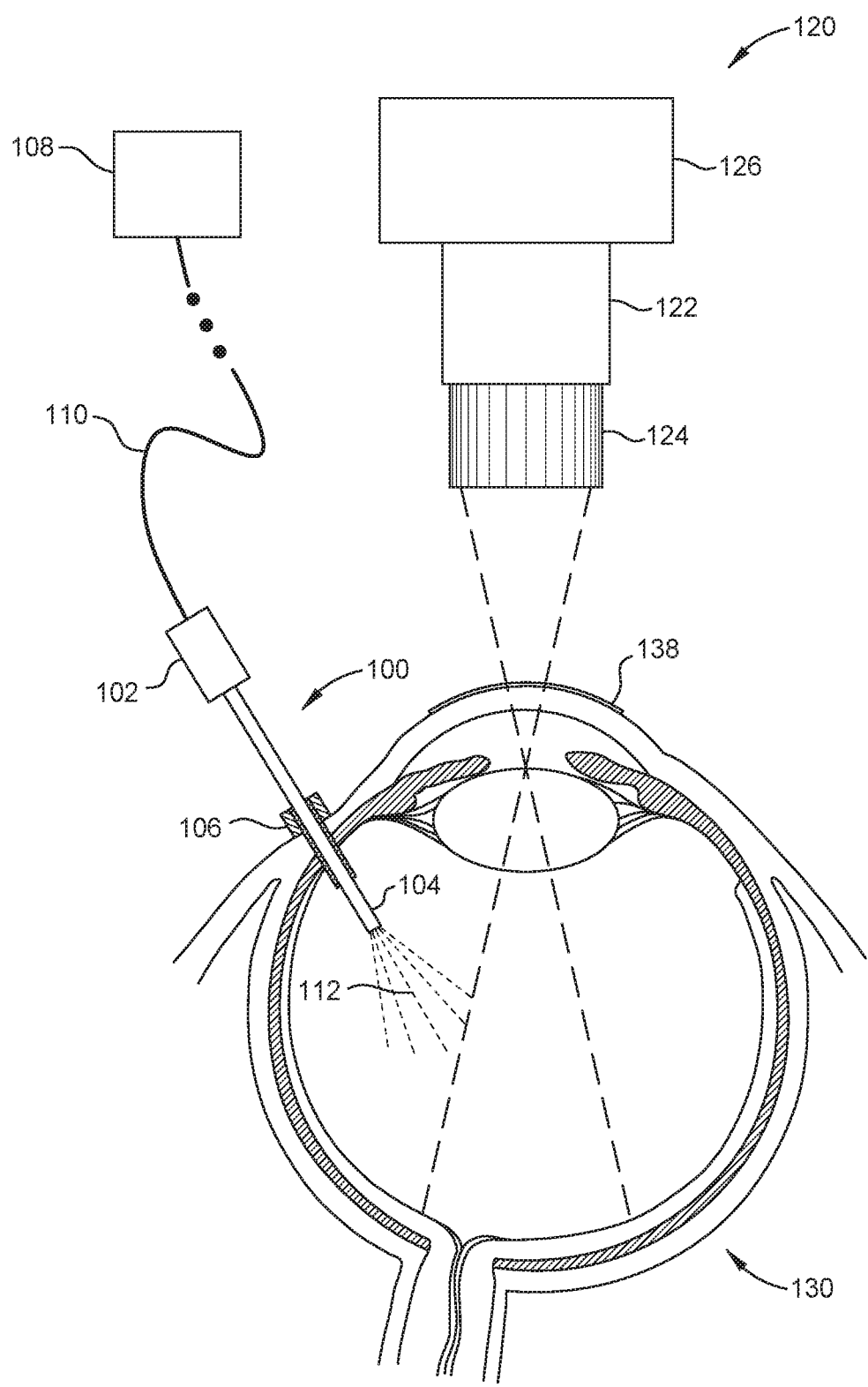
FIG. 1 illustrates a side view of an endoilluminator emitting light onto a retinal region of an eye for viewing by a microscope, according to some embodiments of the present disclosure.

FIG. 1 illustrates a cross-sectional view of an eye 130 having an endoilluminator 100 inserted therein to provide a source of light for viewing by a microscope 120. The endoilluminator 100 includes a handpiece 102 coupled to the proximal end of a shaft or "tube" 104. The handpiece 102 is configured to provide a user (e.g., an ophthalmic surgeon) with a graspable portion of the endoilluminator 100 to provide the surgeon a means for manipulating the depth and location of the tube 104 within the eye 130, and for directing the emitted light 112. Tube 104 is a substantially hollow stainless steel shaft or hypodermic tubing, configured to be inserted into the eye 130 via a cannula and sclerotomy 106. In some examples, the tube 104 is fixedly coupled to the handpiece 102. In another example, the tube 104 is rotatable relative to the handpiece 102. That is, the handpiece 102 includes a circular cross section configured to be rotatably coupled to the tube 104 such that the surgeon can rotate the tube 104 to adjust the incidence of polarized light on the eye 130. In another example, the handpiece 102 is fixedly coupled to the tube 104 such that the surgeon can rotate the tube 104 by rotating the handpiece 102. Although the tube 104 of FIG. 1 is illustrated as a straight shaft, other embodiments include a tube 104 having other shapes. For example, a portion of the tube 104 may be curved to provide light to regions of the eye that would be difficult to illuminate with a straight tube 104. In some embodiments, the endoilluminator 100 and its components are an instrument kit for use in ophthalmic surgery.

The endoilluminator 100 is further configured to house one or more optical fibers (see, for example, FIGS. 2A and 3A, 4, and 5) configured to direct light out of a distal end of the tube 104. For example, the optical fibers may include an optical fiber array (e.g., a plurality of optical fibers in regular linear arrangement or 2-dimensional pattern arrangement) and/or a multi-core optical fiber (e.g., a single-mode (SM) or multi-mode (MM) fiber with multiple cores). In particular, the hollow portion of the tube 104 includes an interior compartment configured to house the optical fiber(s). The optical fibers may include one or more of a polarization maintaining fiber, a polarizing fiber, and/or any other fiber suitable for transmission of light. The polarization maintaining fiber maintains an existing polarization direction that is aligned with a birefringence axis of the fiber, and is capable of maintaining a polarization direction. Similarly, an optical fiber can be stressed (e.g., lateral pressure on the wire) to induce a birefringence axis in order to maintain the polarization of light passed through the fiber.

In contrast, a polarizing fiber may receive polarized or unpolarized light, and propagate the light in one polarization direction while preventing propagation of the light in all other directions. For example, the polarizing fiber may receive transmitted light and filter an incident component (i.e., prevent emission of the incident component of light by reflection or absorption) while emitting a polarized component of the transmitted light. Accordingly, polarizing fibers can polarize, maintain polarization, and/or change direction of already polarized light being propagated through the fibers.

The endoilluminator's handpiece 102 is removably coupled to a distal end of an optic cable 110 having a proximal end coupled to a light source 108. In some embodiments, the light source 108 drives unpolarized light into the entry-point of the optic cable 110, which provides the light to the optical fibers of the endoilluminator 100. In such embodiments, the endoilluminator 100 is configured to polarize the unpolarized light. For example, in some embodiments, the endoilluminator 100 is configured to filter unpolarized light (e.g., using polarizing fibers, a polarizer element, a polarizing filter, etc.) received from the optic cable 110 such that the emitted light 112 is polarized in a certain direction. For example, the endoilluminator 100 filters the light received by the optic cable 110 into linearly, circularly, or elliptically polarized light.

In some embodiments, the light source 108 drives linearly, circularly, or elliptically polarized light into the optic cable 110. In such embodiments, the optic cable 110 and/or the endoilluminator 100 may include polarization maintaining optical fibers configured to maintain the polarization direction of the light in the optic cable 110. Also, in some embodiments, the endoilluminator 100 may be configured to change the polarization of the received polarized light.

It should be noted that in some embodiments, light source 108 is not external to the handpiece 102. For example, in certain embodiments, the handpiece 102 contains light source 108 within a housing or structure of the handpiece 102. For example, light source 108 may include a laser, light emitting diode (LED), or other source of light suitable for ophthalmic surgery.

As shown, the emitted light 112, which is polarized, illuminates the interior of the eye 130, thereby allowing the interior to be viewed with a microscopy system 120. The microscopy system 120 may include any microscope suitable for ophthalmic surgery, including an operating microscope or a digital visualization system. In the example shown, the microscopy system 120 includes a microscope body 126, an objective 122, and a polarization filter 124. The microscope body 126 may be configured as a controller (see FIG. 6) for a digital visualization system, or a housing (see FIG. 7) for an operating microscope. In some examples, the polarization filter 124 is fixedly coupled to the microscopy system 120. In other examples, the polarization filter 124 is rotatably adjustable. The polarization filter 124 can be adjusted by a surgeon to block certain instances of light causing reflection and glare. For example, the polarization filter 124 may be configured to add a 90 degree angle to received light. That is, by adjusting the filter 124, certain instances of light can be blocked (e.g., light reflections/glare).

In the embodiment shown, a contact lens 138 is placed in contact with the cornea of the eye. The contact lens 138 operates as an improved condensing lens device for conveyance of the emitted light 112 through the pupil and into the microscopy system 120. The contact lens 138 can act to form a wide field image of the eye 130. It should be noted that the contact lens 138 is not necessary if a non-contact viewing system is utilized.

Accordingly, as shown in FIG. 1, the endoilluminator 100 polarizes or maintains polarization of light received from the light source 108, and emits the polarized light 112 into the eye 130. In this example, the emitted light 112 is conveyed to the microscopy system 120 through the contact lens 138 and filtered by the polarization filter 124 prior to entering the objective 122. However, it should be noted that in certain embodiments the location of the polarization filter 124 may vary. For example, the polarization filter 124 may be located between the objective 122 and the microscope body 126, or housed within the objective 122 or microscope body 126. In another example, the polarization filter 124 is located at one or more viewing portions (e.g., one or more ocular components of a binocular viewing body) of the microscopy system 120 to provide the surgeon with the ability to adjust the angle of polarization with relative ease.

Accordingly, the surgeon is provided a means for adjusting the polarization filter 124 to block certain instances of light to eliminate glare and reflections, thereby providing a surgeon with a clear visualization of the vitreous, retina and pathology of an eye without having to significantly reduce the amount of light available for surgery.

FIG. 2A illustrates a side perspective view of an exemplary endoilluminator 200, according to some aspects of the disclosure. In the example shown, the endoilluminator 200 includes a first bundle 204a of optical fibers contained within the handpiece 102 and a second bundle 204b of optical fibers contained within the tube 104. In this example, the first bundle 204a of optical fibers receive light from the light source 108 via the optic cable 110 before propagating the light to the second bundle of fibers 204b. In some embodiments, one or more of the optical fibers have a diameter of 0.5 millimeters, although other suitable dimensions are contemplated. Note that although a three-fiber bundle is illustrated and described in examples throughout the disclosure, a bundle of optical fibers may include any suitable number of optical fibers, including one.

The first bundle 204a is separated from the second bundle 204b by a polarizer element 202 configured to receive and polarize light propagated by the first bundle 204a. The polarized light is then passed to the second bundle 204b and emitted as light 112 from the distal end of tube 104. The polarizer element 202 can include any linear polarizer (e.g., absorptive polarizers, beam-splitting polarizers, etc.), circular polarizer (e.g., quarter wave plate), elliptical polarizer, or combination of the three. The polarizer element 202 can be implemented as an in-line fiber optic polarization filter configured to optically couple an optical fiber from the first bundle 204a to a corresponding optical fiber from the second bundle 204b. For example, the in-line polarizer may be positioned between and optically couple a first portion of an optical fiber and a second portion of the optical fiber. In some examples, the polarizer element 202 is implemented by abutting the first bundle 204a and second bundle 204b of optical fibers directly against the polarizer element 202.

In some embodiments, the first bundle 204a is configured to receive polarized light having linear polarization, and to propagate the light to the polarizer element 202. In one example, the polarizer element 202 may include a quarter-wave plate configured to transform the linearly polarized light into a left or right circularly or elliptically polarized light, and propagate the circularly polarized light to the second bundle 204b. In some examples, the optical fibers of the second bundle 204b include polarization-maintaining fibers configured to maintain the polarization of the light received from the polarizer element 202 and propagate the polarized light through the distal end of tube 104.

In some embodiments, the first bundle 204a is configured to receive and propagate unpolarized light to the polarizer element 202. In one example, the polarizer element 202 may include a light filter configured to filter the received light and output linearly polarized light. Similar to embodiments discussed above, the optical fibers of the second bundle 204b may include polarization-maintaining fibers configured to maintain the linear polarization of the light received from the polarizer element 202 and propagated through the length of the tube 104.

In another embodiment, the first bundle 204a of optical fibers is configured to receive and propagate unpolarized light to the second bundle 204b. The second bundle 204b includes polarizing optical fibers configured to polarize the light received from the first bundle 204a. In such an embodiment, the element 202 may not include polarizing capabilities because the second bundle 204b itself is able to polarize the unpolarized light received from the first bundle 204a. Examples of polarizing fibers are described in more detail below in reference to FIGS. 3A and 3B.

FIG. 2B illustrates a cross-sectional view of an example polarization-maintaining fiber 210 that can be used in the bundle of optical fibers shown in FIG. 2A. The example shown is a polarization-maintaining and absorption-reducing (PANDA) fiber having two stress rods 214 on either side of a hollow/solid core 212.

FIG. 2C illustrates a cross-sectional view of an example of a photonic crystal polarization maintaining fiber 220 that can be used in one or more of the first bundle 204a and second bundle 204b of optical fibers. The polarization maintaining fiber 220 includes regularly spaced air holes 222 defined by a micro-structured cladding disposed about a core 224 of the fiber. In other embodiments, suitable polarization maintaining fibers may include bow-tie and elliptical-clad fibers, as well as other hollow/solid-core fibers.

Although in FIG. 2A a polarizer element 202 couples the first bundle 204a and the second bundle 204b, in some embodiments, only one bundle with one or more fibers may be used, the bundle having a distal end that terminates at the distal end of tube 104 and a proximal end that connects to the light source 108. In such embodiments, the light source 108 may, for example, emit polarized light into the bundle, which may include one or more polarization maintaining fibers (e.g., FIGS. 2B and 2C). In another example, the light source 108 may emit unpolarized light into the bundle, which may include polarizing fibers (e.g., FIGS. 3A-3B).

Figure 3A:
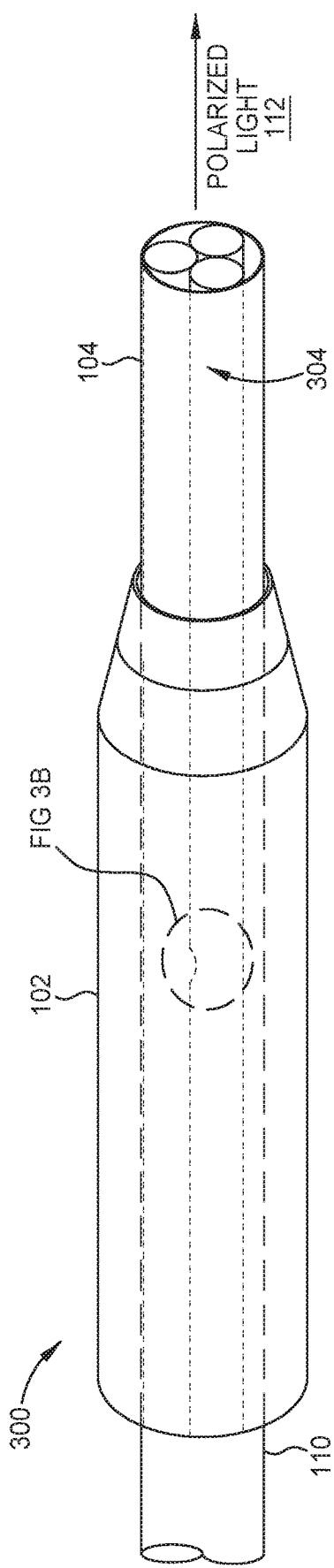
FIG. 3A illustrates a side perspective view of an endoilluminator, according to some embodiments of the present disclosure.

FIG. 3A illustrates a side perspective view of an endoilluminator 300 including a bundle 304 of polarizing optical fibers, according to some aspects of the disclosure. That is, the polarizing optical fibers polarize the received light, or change or maintain direction of received polarized light. In the embodiment shown, the bundle 304 of fibers is contained within handpiece 102 and tube 104, and configured to receive light from the light source 108 via optic cable 110. The bundle 304 of fibers polarizes the received light and propagates the polarized light to a distal end of the tube 104 where the light 112 is emitted.

In the example shown, one or more of the fibers in the bundle 304 include an indention or a notch 306 in the outer surface of the fiber caused by modification of air holes (e.g., air holes 308 of FIG. 3B) inside of the fiber. In some examples, the bundle 304 of fibers includes a photonic crystal type of fiber illustrated in FIG. 2C. In some examples, the optical fibers include an air-silica hollow core photonic bandgap type fiber. In other examples, the fibers in bundle 304 may include any other fiber types suitable for polarizing and emitting light 112, including: side polished or "half-coupler" fibers, D-shaped fibers, or solid-core index-guiding photonic crystal fibers having long-period grating.

Figure 3B:
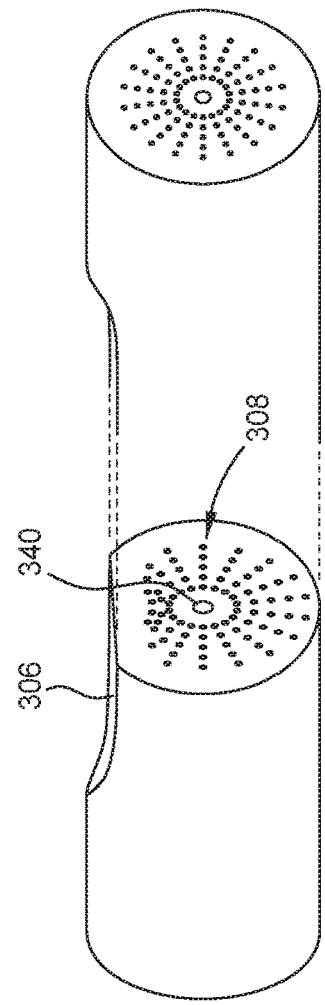
FIG. 3B illustrates a side perspective and cross-sectional view of a portion of a fiber optic element in the endoilluminator of FIG. 3A, according to some embodiments of the present disclosure.

As shown in FIG. 3B, the notch 306 may be caused by heating and/or compression of the fiber such that air holes 308 inside of the fiber change in the size, shape, location, or completely/partially collapse. In the example shown, the air holes 308 are disposed about a hollow core 340 within the optical fiber. In some embodiments, the modification is performed by applying high frequency laser pulses to the one side of the fiber. Modifying the air holes 308 in this way results in an asymmetric waveguide structure that functions to polarize light propagated through the structure by leaking a first polarization out of the fiber while maintaining the propagation of a second polarization along the length of the fiber, where the second polarization is orthogonal to the first polarization. That is, the notched fibers can be utilized to polarize light received from an unpolarized source, directionally polarize an already polarized source of light, or maintain a direction of polarized light.

In some embodiments, the light source 108 provides unpolarized light which is received by the endoilluminator 300 via the optic cable 110. Accordingly, the bundle 304 of fibers polarize the received light and maintain the polarization while propagating the polarized light to the distal end of the tube 104 where the light 112 is emitted.

In some embodiments, the light source 108 provides polarized light which is received by the endoilluminator 300 via the optic cable 110. In such an embodiment, the bundle 304 of polarization fibers can maintain and/or change the polarization of the received light. In one example, bundle 304 of polarization fibers receive linearly polarized light from the light source 108. In this example, the bundle 304 of polarization fibers is configured to circularly or elliptically polarize the received light, and maintain the circular polarization of the light as it is propagated through the endoilluminator 300. Alternatively, the bundle 304 of polarization fibers are configured to maintain the linear polarization of the light received from the light source 108 as it is propagated through the endoilluminator 300 to the distal end of the tube 104 where the light 112 is emitted.

FIG. 4 illustrates a side perspective view of an endoilluminator 400 that includes a polarizing filter 402 at the tip of the tube 104, according to some aspects of the disclosure. The endoilluminator 400 contains a bundle 404 of three optical fibers configured to receive polarized or unpolarized light from the light source 108 via optic cable 110. The optical fibers propagate the light to a distal end of the tube 104 where the polarizing filter 402 polarizes and emits the light 112.

In one example, the polarizing filter 402 includes an absorptive polarizer configured to selectively absorb light in one or more polarization states. Such an absorptive polarizer may include an absorptive dye color filter array or a polarized red, green, and blue (RGB) light color filter array similar to those used in most liquid crystal displays. The absorptive polarizer may include any suitable dichroic film and/or dye material known to those of skill in the art.

In another example, the polarizing filter 402 includes an electronic polarizer such as a wire grid polarizer. In general, wire grid polarizers will reflect a first direction of light utilizing an electric field vector parallel to the wires of the grid, and transmit a second direction of light utilizing an electric field vector perpendicular to the wires of the grid. That is, the wire grid polarizer will function as a mirror for the first direction of light, and will act transparent for the second direction of light.

FIG. 5 illustrates a side perspective view of an endoilluminator 500 having a chandelier probe 502 configured to emit polarized light according to some aspects. A chandelier probe 502 is useful in illuminating a large area of a surgery site. In ophthalmic surgery, and in particular in vitreo-retinal surgery, it is desirable to view as large a portion of the retina as possible. Thus, a chandelier probe is sometimes inserted through a small incision hole in the sclera or a cannula and sclerotomy 106.

In this example, the endoilluminator 500 receives light from the light source 108 and propagates the light via an optical fiber 504 contained within the handpiece 102 and tube 104, to the chandelier probe 502. In some examples, the chandelier probe 502 has a proximal end abutting the optical fiber 504 and a tapered section emitting light at its distal end. In some other embodiments, the chandelier probe 502 is a portion of the optical fiber 504 that extends outward from the distal end of the tube 104. Although FIG. 5 illustrates an endoilluminator 500 including only one optic fiber 504, any suitable number of optical fibers are within the scope of the disclosure.

In some embodiments, the chandelier probe 502 includes a polarizing filter similar to that described above in FIG. 4. In this example, the chandelier probe 502 receives polarized or unpolarized light from the optical fiber 504, and emits polarized light 112 according to the filter configuration of the polarizing filter. For example, the chandelier probe may include a dichroic film and/or dye material or a wire grid polarizer.

In some embodiments, the chandelier probe 502 does not include a polarizing mechanism, but rather is coupled to the distal end of the tube 104 of the endoilluminator shown in FIGS. 2A and 3A. In such an embodiment, the chandelier probe 502 emits light 112 that has been polarized prior to emission.

Note that the arrangement or positioning of the distal ends of bundles 204b and 304, filter 402, and chandelier 502 with respect to the distal end of tube 104, as shown in FIGS. 2A-5, is merely exemplary. For example, although FIGS. 2A-5 show the distal end of tube 104 being flush with the distal ends of bundles 204b and 304, in some embodiments, the distal end of tube 104 may extend beyond the distal ends of bundles 204b and 304. In such embodiments, one or more components (e.g., lens and/or protective component) may be placed at the distal end of bundles 204b and 304. Similarly, in some embodiments, the distal end of tube 104 may extend beyond the distal end of filter 402 and one or more components may be placed at the distal end of filter 402. Also, in some embodiments, the distal end of tube 104 may be flush with or extend beyond the distal end of chandelier 502.

Figure 6:
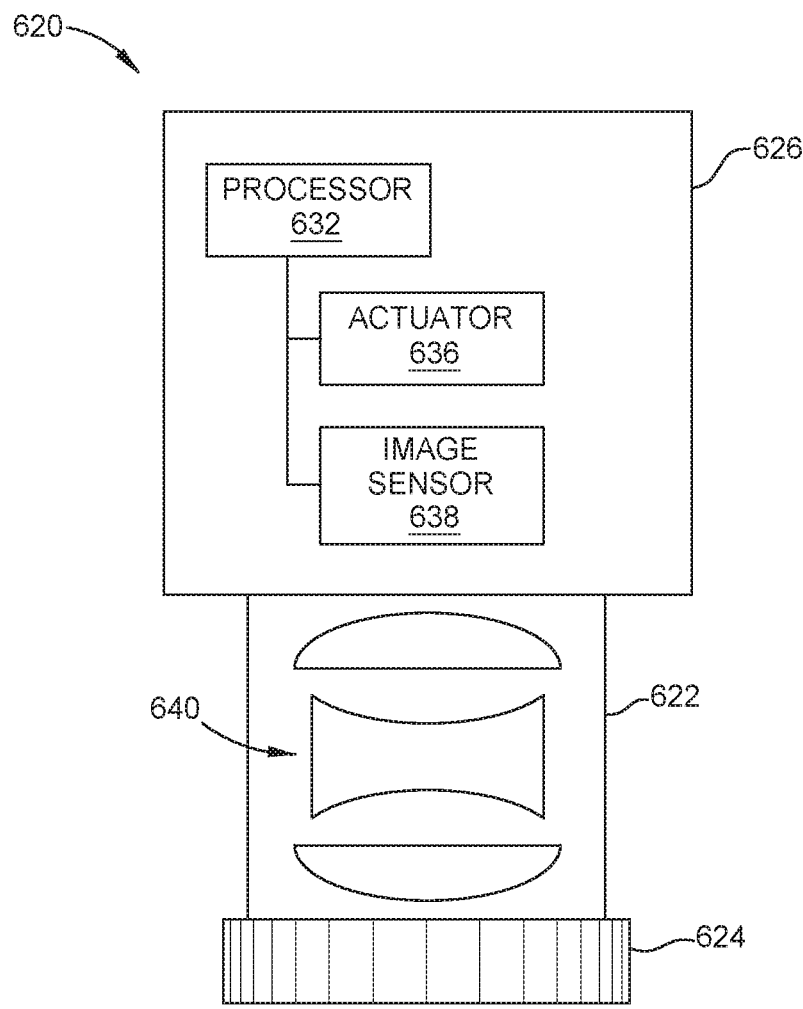
FIG. 6 illustrates a block diagram of a digital visualization system with a polarizing filter, according to some embodiments of the present disclosure.

FIG. 6 illustrates a block diagram of an example digital visualization system 620 according to some aspects. Those skilled in the art will appreciate that a digital visualization system can include more or fewer components than the simplified system described herein. The digital visualization system 620 described herein includes only those components useful for describing some prominent features of implementations within the scope of the claims.

The digital visualization system 620 includes an objective 622 containing one or more optical lenses 640, a controller 626 configured to control a focusing function of the objective 622, and a polarization filter 624 configured to polarize light prior to being received by the objective 622. In some examples, the polarization filter 624 is fixedly coupled to the digital visualization system 620. In other examples, the polarization filter 624 is rotatably adjustable. The location of the polarization filter 624 may vary in terms of its location within the digital visualization system 620 and still be within the scope of this disclosure. For example, the polarization filter 624 may include an electronic polarizer such as a wire grid polarizer configured for electromechanical adjustment by the surgeon. In some examples, a wire grid polarizer may be located within the controller 626 and configured to pass polarized light onto the image sensor 638.

In the embodiment shown, the controller 626 includes the processor 632 communicatively coupled to an actuator 636 and one or more electronic image sensors 638. For example, the microscopy system 120 may include a single image sensor 638 or a pair of image sensors 638, either of which may be utilized to provide a stereoscopic view. An image sensor 638 described herein may be implemented on a variety of different photosensitive devices. These include general purpose or special purpose image sensors, environments, or configurations. Examples of image sensors, environments, and configurations that may be suitable for use with the invention include, but are not limited to, semiconductor charge-coupled devices (CCD) or active sensor elements in CMOS (Complementary metal-oxide-semiconductor) or N-Type metal-oxide-semiconductor (NMOS) technologies, all of which can be germane in a variety of applications including, but not limited to digital operating microscopes and digital visualization systems for ophthalmic surgery.

The image sensor 638 may receive the light emitted from an endoilluminator (and reflected out of an eye during an ophthalmic surgery) and convert the light into an electronic signal made up of image statistics for each frame, wherein each frame is composed of a single static image. The image statistics can be manipulated by focusing the optical lenses 640 of the objective 622 and/or by rotating or adjusting the polarization filter 624.

In some embodiments, the surgeon can electronically adjust the polarization filter until glare is minimized by toggling a switch or push-button means for activating the actuator 636. In one example, the actuator 636 is configured to iteratively rotate the polarization filter 624 into discrete positions. This provides the surgeon with the ability to determine a position the polarization filter 624 that results in the least amount of glare or light reflection.

In some embodiments, the polarization filter 624 is manually rotatable by the surgeon. For example, the surgeon may rotate or adjust the polarization filter 624 by hand to block certain instances of light and eliminate glare and reflections observed through the microscopy system 620.

Figure 7:
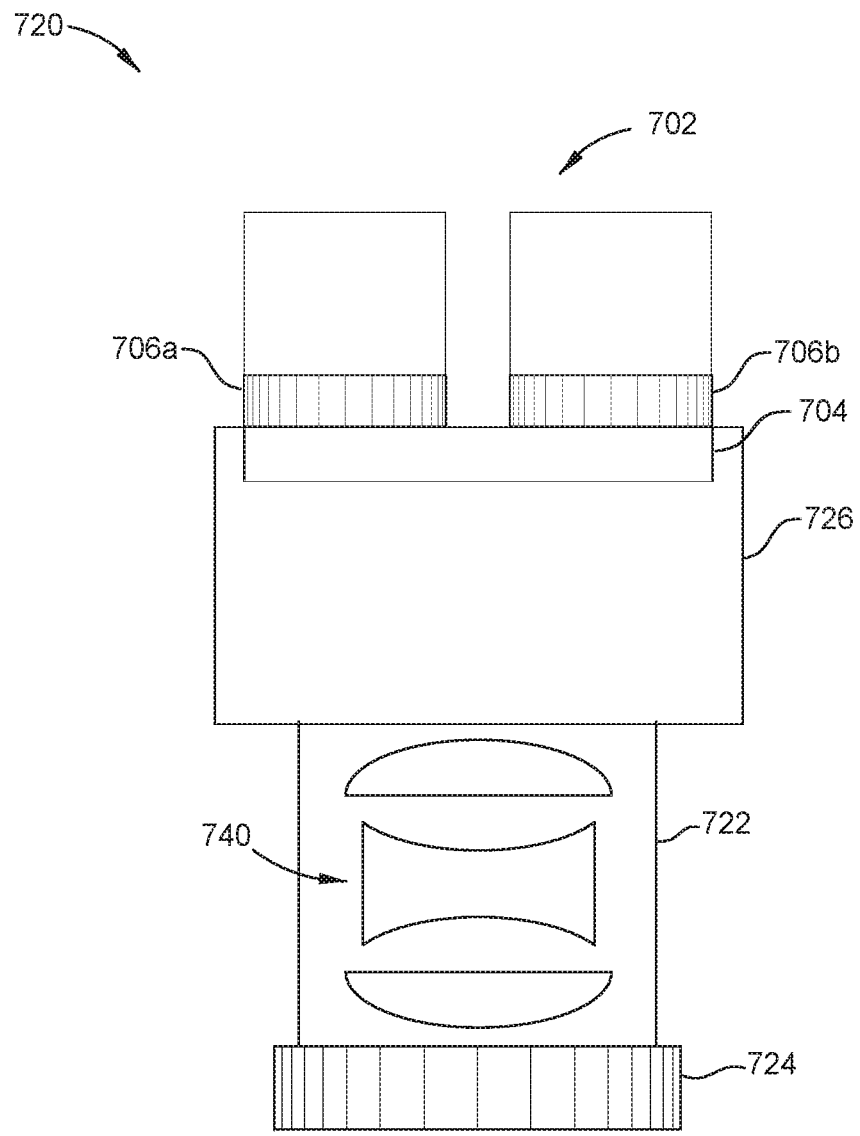
FIG. 7 illustrates a block diagram of an operating microscope with a polarizing filter, according to some embodiments of the present disclosure.

FIG. 7 illustrates a block diagram of an example operating microscope 720 according to some aspects. Those skilled in the art will appreciate that an operating microscope can include more or fewer components than the simplified system described herein. The operating microscope 720 described herein includes only those components useful for describing some prominent features of implementations within the scope of the claims.

The operating microscope 720 includes an objective 722 containing one or more optical lenses 740, a viewing element 702, and a housing 726. Although FIG. 7 illustrates an example operating microscope 720 having a binocular viewing element 702, other suitable configurations, such as a monocular viewing element 702, are within the scope of this disclosure.

In one embodiment, operating microscope 720 includes one or more polarization filters 706a and 706b. In some examples, one or more of the polarization filters 706a and 706b are fixedly coupled to the operating microscope 720. In other examples, one or more of the polarization filters 706a and 706b are configured to be manually rotatable by the surgeon at the viewing element 702. In one example, the housing 726 includes an adjusting mechanism 704 configured to provide the surgeon with a means for manually rotating both polarization filters 706a and 706b simultaneously. In another example, each polarization filter 706a and 706b may be individually adjustable.

In another embodiment, operating microscope 720 includes one or more polarization filters 724 at the objective 722. In some examples, the polarization filter 724 is fixedly coupled to the objective and/or housing 726. In other examples, the polarization filter 724 is manually rotatable by the surgeon. It should be noted that the polarization filter 724 may be located in any suitable position with respect to the objective 722. For example, the polarization filter 724 may be located at the distal end of the objective 722, within the objective 722, or at a proximal end of the objective 722.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims. Those skilled in the art will appreciate that the endoilluminators illustrated in FIGS. 1, 2A, 3A, 4, and 5 can include more components than the simplified illustrations described herein. The endoilluminators described herein include only those components useful for describing some prominent features of implementations within the scope of the claims.

What is claimed is:

1. An endoilluminator for ophthalmic surgery, comprising:
    a tube comprising an interior compartment between a proximal end and a distal end of the tube, wherein the distal end of the tube is configured to be inserted into an eye;
    a handpiece coupled to a light source and the proximal end of the tube, wherein the endoilluminator is configured to filter an incident component of light transmitted by the light source and emit a polarized component of the transmitted light through the distal end of the tube; and
    an optical fiber contained within the interior compartment, the optical fiber configured to receive the light transmitted by the light source and transmit the received light through the tube, wherein the optical fiber comprises an indention along an outer surface of the optical fiber, and wherein the indention is configured to polarize the received light.

2. The endoilluminator of claim 1, wherein the handpiece comprises the light source configured to generate the transmitted light.

3. The endoilluminator of claim 1, wherein the optical fiber is configured to emit the polarized component of the transmitted light through a distal end of the optical fiber.

4. The endoilluminator of claim 3, further comprising a light-polarizing filter configured to optically couple a first portion of the optical fiber with a second portion of the optical fiber.

5. The endoilluminator of claim 4, wherein the light-polarizing filter is configured to:
receive, via the first portion of the optical fiber, the light transmitted by the light source;
filter the incident component of the transmitted light; and
transmit the polarized component of the transmitted light into the second portion of the optical fiber.

6. The endoilluminator of claim 5, wherein the second portion of the optical fiber comprises a polarization-maintaining optical fiber configured to maintain the polarized component of the transmitted light.

7. The endoilluminator of claim 4, wherein the light-polarizing filter comprises an in-line fiber optic polarization filter.

8. The endoilluminator of claim 3, wherein the optical fiber is configured to filter the incident component of the transmitted light.

9. The endoilluminator of claim 8, wherein the optical fiber comprises regularly spaced air holes disposed about a core of the optical fiber.

10. The endoilluminator of claim 3, further comprising a chandelier probe coupled to the distal end of the optical fiber, and located at the distal end of the tube.

11. The endoilluminator of claim 1, further comprising:
a first polarizing element and a second polarizing element within the interior compartment, the first polarizing element being configured to polarize the incident component of light transmitted by the light source and emit the first polarized component of the transmitted light, and the second polarizing element being configured to polarize the first polarized component of the transmitted light and emit a second polarized component of the transmitted light.

\* \* \* \* \*